United States Patent [19]

Byron et al.

[11] Patent Number: 5,508,023

[45] Date of Patent: Apr. 16, 1996

[54] PHARMACEUTICALLY ACCEPTABLE AGENTS FOR SOLUBILIZING, WETTING, EMULSIFYING, OR LUBRICATING IN METERED DOSE INHALER FORMULATIONS WHICH USE HFC-227 PROPELLANT

[75] Inventors: Peter Byron; Frank Blondino, both of Richmond, Va.

[73] Assignees: The Center for Innovative Technology, Herndon; Virginia Commonwealth University, Richmond, both of Va.

[21] Appl. No.: 226,041

[22] Filed: Apr. 11, 1994

[51] Int. Cl.$^6$ .................................................. A61K 9/12
[52] U.S. Cl. ........................ 424/45; 424/46; 514/937
[58] Field of Search .................... 424/45, 46; 514/937

[56] References Cited

U.S. PATENT DOCUMENTS

| | | | |
|---|---|---|---|
| 5,118,494 | 6/1992 | Schultz et al. | 424/45 |
| 5,225,183 | 7/1993 | Purewal et al. | 424/45 |

FOREIGN PATENT DOCUMENTS

| | | |
|---|---|---|
| 0372777A2 | 6/1990 | European Pat. Off. . |
| 11744 | 6/1993 | WIPO . |

OTHER PUBLICATIONS

Morén, F. et al. (1993). Aerosols in Medicine. Principles, Diagnosis and Therapy. Elsevier Sci. Pub., pp. 303–319.
Martin et al., Physical Pharmacy, 3rd Ed., Lea & Febiger, Philadelphia, PA, 1983, pp. 452–455.

Martin et al., Physical Pharmacy, 3rd Ed., Lea & Febiger, Philadelphia, PA, 1983, pp. 544–573.

Whitham et al., "Alternative Propellants: Proprietary Rights, Toxicological Issues and Projected Licensing Problems"; Respiratory Drug Delivery IV, 1994, pp. 203–209.

Dalby et al., "CFC Propellant Substitution: P–134a as a Potential Replacement for P–12 in MDIs"; Pharmaceutical Technology, Mar. 1990, pp. 32–39.

*Primary Examiner*—Thurman K. Page
*Assistant Examiner*—Raj Bawa
*Attorney, Agent, or Firm*—Whitham, Curtis, Whitham, & McGinn

[57] ABSTRACT

1,1,1,2,3,3,3-heptafluoropropane (HFC-227) has been identified as a highly polar propellant. Surfactants which have an elevated value (9.6 or greater) for their hydrophilic-lipophilic balance (HLB) can be used as suspending, wetting, and lubricating agents or cosolvents in metered dose inhaler (MDI) formulations pressurized with HFC-227 or propellant blends that contain HFC-227. Particularly preferred surfactants include polyoxyethylene sorbitan monolaurate, polyoxyethylene sorbitan mono-oleate, polyethylene glycol 300, propoxylated polyethylene glycol, polyoxyethylene 4 lauryl ether, and diethylene glycol monoethyl ether.

20 Claims, No Drawings

PHARMACEUTICALLY ACCEPTABLE AGENTS FOR SOLUBILIZING, WETTING, EMULSIFYING, OR LUBRICATING IN METERED DOSE INHALER FORMULATIONS WHICH USE HFC-227 PROPELLANT

BACKGROUND OF THE INVENTION

1. Field of the Invention

The invention is generally directed at metered dose inhaler (MDI) formulations which utilize non-ozone depleting propellants. More specifically, the invention is directed to MDI formulations which include 1,1,1,2,3,3,3-heptafluoropropane (HFC-227) as a propellant.

2. Description of the Prior Art

There are two types of formulations administered using pressurized MDIs. In conventional solution-type MDIs, drug is dissolved with the aid of non-volatile co-solvents such as ethanol. Conversely, in suspension formulations, small micronized particles of undissolved drug are distributed in the propellant or propellant blend. When a patient actuates the valve, a precisely measured dose of a drug is released and subsequently inhaled. Large particles or droplets in the spray impact in the oropharynx. By contrast, smaller particles (1–10 μm) are required for penetration into the bronchioles or pulmonary regions of the lung. It is therefore necessary that suspension-type MIDIs be formulated with "potentially respirable" micronized particles (median diameter of approximately 3 μm) and that these particles do not grow during the shelf life of the product. Growth can lead to less penetration of drug into the lung and disrupt operation of the metering valve.

Surface active compounds or "surfactants" are used in MDI formulations to aid in the dissolution or suspension of the drug in the propellant or propellant blend. The surfactants also serve to improve valve function by virtue of their lubricating properties. In order to achieve these objectives however, the surfactant must be dissolved in sufficient concentrations. For example, surfactant should ordinarily be at approximately 0.01–5% weight in volume (w/v). Often, the surfactant is incorporated at about 1/10th the concentration of the drug in the MDI formulation.

Currently, chlorofluorocarbon (CFC) blends are used as propellants in MDIs. CFC-11, CFC-12, and CFC-114 are the most widely used propellants in MDI formulations. However, use of CFC substances has come under criticism in recent years because they are widely believed to be damaging to the Earth's ozone layer. The Montreal Protocol on Substances that Deplete the Ozone Layer is an international treaty that has been signed by most industrialized countries and it prescribes a gradual phase out of CFC substances by the end of 1995. The treaty restrictions are a difficult burden on the MDI industry since no suitable propellants have been identified as "drop-in" replacements for CFCs, in that they would require little or no modification to drug formulations, formulating techniques, and materials used in MDIs.

Two hydrofluorocarbon (HFC) gases, 1,1,1,2-tetrafluoroethane (134a) and 1,1,1,2,3,3,3-heptafluoropropane (227), are currently considered as the most viable CFC alternatives for use in MDIs. However, because these two excipients have not been assessed or approved by any government authority, they must undergo the same degree of toxicological testing which is required for any new drug substance. The International Pharmaceutical Aerosol Consortiums for Toxicology Testing (IPACT-I for 134a and IPACT-II for 227) have been organized to test the HFCs and compile a safety data package suitable for satisfying the leading health authorities around the world. Members of these consortia will be able to reference the compiled data package for each excipient. However, they will be required to perform bridging studies on their own reformulated MDI products.

The reformulation of MDIs with alternative propellants requires a variety of criteria to be met. First, the drug should be easily dissolved or dispersed within the propellant. Partial dissolution, however, can result in problems with crystal growth over time. Uniform distribution of the drug within the propellant assures that the drug dose administered per each actuation is constant. Second, the surfactant should dissolve within the propellant or propellant blend at the required concentration. Third, if a blend of propellants is used, the blend should be single phase at room temperature. Fourth, the particle size of the drug following spraying should duplicate the size patterns which are now available with CFCs so that the new formulations are at least as efficacious as those currently in use. Fifth, the MDI formulation (e.g., surfactant and propellant or propellant blend) should be compatible with the elastomer seals and valve components used in the MDI canister to prevent leakage which results from shrinking and to prevent valve jamming which results from swelling. Sixth, the MDI formulation should be physically and chemically stable for an extended period of time. Seventh, for suspension formulations, the drug should be readily dispersed after standing. Eighth, for suspension formulations, the suspension should remain homogenous for the period between shaking, firing, and releasing the valve so as to refill the metering chamber.

SUMMARY OF THE INVENTION

It is an object of this invention to provide MDI formulations which utilize HFC-227 as the sole propellant or use HFC-227 in a propellant blend with a pharmaceutically acceptable surfactant for suspending, solubilizing, wetting, emulsifying, or lubricating.

According to the invention, it has been discovered that HFC-227 is a highly polar propellant, and that prior assumptions that HFC-227 has extreme lipophilicity are completely incorrect. Thus, polar surfactants which have a high hydrophile-lipophile balance (HLB) such as polyoxyethylene sorbitan monolaurate (Tween 20), polyoxyethylene sorbitan mono-oleate (Tween 80), polyethylene glycol 300 (PEG 300), Antarox 31R1, Brij 30, and Transcutol can be used effectively in MDI formulations which include HFC-227 as the sole propellant or include HFC-227 in a propellant blend, such as, for example, an HFC-227/HFC-134a blend.

DETAILED DESCRIPTION OF THE PREFERRED EMBODIMENTS OF THE INVENTION

Conventional wisdom in the search for non-CFC propellants for use in MDI formulations has been that HFC-227 is a poor solvent. This is because HFC-227 fails to dissolve the commonly used MDI surfactants sorbitan mono-oleate (Span 80), sorbitan trioleate (Span 85), oleic acid, and lecithin, in useful concentrations without the aid of a cosolvent. Prior to this invention, the vapor pressure of HFC-227, its chemical structure, and miscibility with other hydrophobic propellants like butane were believed to indicate its extreme lipophilicity. The commonly used MDI surfactants noted above are all lipophilic and are characterized by low HLB values (See, Martin et al., *Physical Pharmacy*, 3rd Ed., Lea & Febiger, Philadelphia, Pa., pp. 452–455, 1983).

As explained in *Physical Pharmacy*, an arbitrary scale of values has been developed by Griffin to serve as a measure of the HLB of surfactants. On this scale, surfactants with lower HLB values (1.8 to 8.6) are more lipophilic, while surfactants with higher HLB values (9.6 to 16.7 and above) are more hydrophilic. The HLB of a number of polyhydric alcohol fatty acid esters, such as glyceryl monostearate, may be estimated by using the formula $$HLB=20(1-(S/A))$$

in which S is the saponification number of the ester and A is the acid number of the fatty acid. The HLB of polyoxyethylene sorbitan monolaurate (Tween 20), for which S=45.5 and A=276, is $$HLB=20(1-(45.5/276))=16.7$$

This invention particularly contemplates the use of surfactants having a higher HLB value of 9.6 or greater in MDI formulations which employ HFC-227 alone or in combination with other propellants. Examples of such surfactants include polyoxyethylene sorbitan monolaurate (Tween 20), polyoxyethylene sorbitan mono-oleate (Tween 80), polyethylene glycol 300 (PEG 300), propoxylated polyethylene glycol (Antarox 31R1), polyoxyethylene lauryl ether (Brij 30), and purified diethylene glycol monoethyl ether (transcutol).

Experiments have demonstrated that HFC-227 is miscible in all proportions with 99.9% ethanol. Since ethanol is a fairly polar solvent, this finding indicates that the assumption that HFC-227 has extreme lipophilicity is completely incorrect. Molecular modeling has been performed which further demonstrates the high polarity of HFC-227.

A number of surfactants were combined with HFC-227. Table 1 demonstrates that a number of polar surfactants dissolve appreciably in liquified HFC-227. This result was completely unpredictable and surprising as evidenced by the lack of its discovery to date and the conventional wisdom which stands for the proposition that HFC-227, like HFC-134a, is non-polar. The substances Antarox 31RA, Brij 30, PEG 300, Transcutol, Tween 20, and Tween 80 are all polar surfactants which are commonly employed in aqueous systems. These relatively nontoxic surfactants can be used as suspending, wetting, and lubricating agents or cosolvents in MDI formulations pressurized with HFC-227.

TABLE 1

APPARENT SOLUBILITY OF VARIOUS SURFACTANTS/SOLUBILIZERS (SAA) IN HFC-227.

| SURFACTANT OR SOLUBILIZER | WEIGHT OF SAA (g) | WEIGHT OF HFC-227 (g) | % w/w | NOTES AT TIME = 0 HRS. (TIME OF MANUFACTURE) TEMP. = 22–23° C. | SOLUBILITY INFORMATION |
|---|---|---|---|---|---|
| AEROSOL-OT (DIOCTYL SODIUM SULFOSUCCINATE) | 0.020 | 65.472 | ≈0.02 | NO APPARENT AFFECT ON THE SAA. TWO PHASE SYSTEM. SAA INSOLUBLE. | APPARENT SOLUBILITY <<0.02 |
| ANTAROX 31R1 (PROPOXYLATED POLYETHYLENE GLYCOL) a | 1.012 | 10.500 | ≈8.8 | CLEAR SOLUTION. | SINGLE PHASE FROM 0–8.8% w/w |
| | 6.727 | 14.327 | ≈32.0 | TWO PHASES PRESENT. | TWO PHASES FROM 8.8–42.4% w/w |
| | 4.745 | 6.451 | ≈42.4 | CLEAR SOLUTION. | |
| | 6.727 | 4.425 | ≈60.3 | CLEAR SOLUTION. | SINGLE PHASE FROM 42.4–100% w/w |
| ARLACEL 60 (SORBITAN MONOSTEARATE) | 0.008 | 74.061 | ≈0.01 | NO APPARENT AFFECT ON THE SAA. TWO PHASE SYSTEM. SAA INSOLUBLE. | APPARENT SOLUBILITY <<0.01 |
| BRIJ 30 (POLYOXYETHYLENE (4) LAURYL ETHER)[a] | 1.034 | 84.862 | ≈1.2 | CLEAR SOLUTION. | SINGLE PHASE FROM 0–1.2% w/w |
| | 1.001 | 9.000 | ≈10.0 | CLOUDY SOLUTION. c,e | TWO PHASES FROM 1.2–25.0% w/w |
| | 1.034 | 6.273 | ≈14.2 | CLEAR SOLUTION. | |
| | 2.499 | 7.491 | ≈25.0 | CLEAR SOLUTION. c,e | |
| | 5.001 | 4.951 | ≈50.3 | CLEAR SOLUTION. b,d | |
| | 7.501 | 2.533 | ≈74.8 | CLEAR SOLUTION. b,d | SINGLE PHASE FROM 25.0–100% w/w |
| | 8.999 | 0.993 | ≈90.1 | CLEAR SOLUTION. c,d | |
| CENTROLEX P (GRANULAR LECITHIN) | 0.009 | 84.693 | ≈0.01 | NO APPARENT AFFECT ON THE SAA. TWO PHASE SYSTEM. SAA INSOLUBLE. | APPARENT SOLUBILITY <<0.01 |
| GLYCOMUL O (SORBITAN MONOOLEATE) | 0.010 | 76.617 | ≈0.01 | SAA MIGRATED TO SIDE OF BOTTLE. TWO PHASE SYSTEM. SAA INSOLUBLE. | APPARENT SOLUBILITY <<0.01 |
| GLYCOMUL SOO (SORBITAN SESQUIOLEATE) | 0.010 | 88.408 | ≈0.01 | SAA MIGRATED TO SIDE OF BOTTLE. TWO PHASE SYSTEM. SAA INSOLUBLE. | APPARENT SOLUBILITY <<0.01 |
| MACOL SA 2 (POLYOXYETHYLENE (2) STEARYL ESTER) | 0.013 | 82.720 | ≈0.02 | NO APPARENT AFFECT ON THE SAA. TWO PHASE SYSTEM. SAA INSOLUBLE. | APPARENT SOLUBILITY <<0.02 |
| OLEIC ACID | 0.014 | 81.419 | ≈0.02 | SAA PRESENT AS SMEAR ON CONTAINER WALL. SAA FLOATING. | APPARENT SOLUBILITY <<0.02 |
| PEG 300 | 0.700 | 86.847 | ≈0.8 | CLEAR SOLUTION. | APPEARS |

TABLE 1-continued

APPARENT SOLUBILITY OF VARIOUS SURFACTANTS/SOLUBILIZERS (SAA) IN HFC-227.

| SURFACTANT OR SOLUBILIZER | WEIGHT OF SAA (g) | WEIGHT OF HFC-227 (g) | % w/w | NOTES AT TIME = 0 HRS. (TIME OF MANUFACTURE) TEMP. = 22–23° C. | SOLUBILITY INFORMATION |
|---|---|---|---|---|---|
| (POLYETHYLENE GLYCOL) | 0.700 | 3.548 | ≈16.5 | CLEAR SOLUTION. | MISICIBLE IN |
|  | 2.096 | 7.527 | ≈21.8 | CLEAR SOLUTION. | ALL |
|  | 7.898 | 6.113 | ≈58.4 | CLEAR SOLUTION. | PROPORTIONS. |
| PEG 8000 (POLYETHYLENE GLYCOL) | 0.008 | 82.348 | ≈0.01 | NO APPARENT AFFECT ON THE SAA. TWO PHASE SYSTEM. SAA INSOLUBLE. | APPARENT SOLUBILITY <<0.01 |
| SPAN 85 (SORBITAN TRIOLEATE) | 0.010 | 82.871 | ≈0.01 | NO APPARENT AFFECT ON THE SAA. TWO PHASE SYSTEM. SAA INSOLUBLE. | APPARENT SOLUBILITY <<0.01 |
| TRANSCUTOL (PURIFIED DIETHYLENE GLYCOL MONOETHYL ETHER) | 0.701 | 88.226 | ≈0.8 | CLEAR SOLUTION. | APPEARS MISCIBLE IN ALL PROPORTIONS. |
|  | 0.701 | 4.465 | ≈13.6 | CLEAR SOLUTION. |  |
|  | 2.002 | 4.195 | ≈32.3 | CLEAR SOLUTION. |  |
|  | 5.019 | 5.895 | ≈48.0 | CLEAR SOLUTION. |  |
| TWEEN 20 (POLYOXYETHYLENE (20) SORBITAN MONOLAURATE) | 0.052 | 97.183 | ≈0.06 | CLEAR SOLUTION. | APPEARS MISCIBLE IN ALL PROPORTIONS. |
|  | 0.066 | 6.660 | ≈1.0 | CLEAR SOLUTION. |  |
|  | 2.124 | 6.113 | ≈25.6 | CLEAR SOLUTION. |  |
| TWEEN 80 (POLYOXYETHYLENE (20) (SORBITAN MONOOLEATE) a | 3.271 | 80.446 | ≈3.9 | THREE PHASES. | THREE PHASES FROM 3.9–10.0% w/w |
|  | 1.000 | 8.966 | ≈10.0 | CLOUDY SOLUTION. c,e |  |
|  | 3.271 | 18.232 | ≈15.2 | TWO PHASES. |  |
|  | 2.500 | 7.545 | ≈24.9 | CLEAR SOLUTION. b,e | TWO PHASES FROM 10.0–24.9% w/w |
|  | 4.999 | 4.961 | ≈50.2 | CLEAR SOLUTION. b,d |  |
|  | 7.500 | 2.539 | ≈74.7 | CLEAR SOLUTION. b,d | SINGLE PHASE FROM 24.9–100% w/w |
|  | 9.000 | 1.023 | ≈89.8 | CLEAR SOLUTION. b,d |  | a Single and multiple phase systems exist when surfactant and HFC-227 are blended in different ratios.
b Appears as a single phase at 4° C.
c Appears as two phases at 4° C.
d Appears as a single phase at 37° C.
e Appears as two phases at 37° C.

In addition to preparing surfactant/HFC-227 blends, various surfactants were combined with 50:50 by weight blends of HFC-227 and HFC-134a. It has been discovered that the propellants HFC-227 and HFC-134a are miscible in all proportions (0.1%–99.9%). In the blends, the surfactant was incorporated at a concentration of ≈0.1%. Table II shows that the solubility of surfactants was greater than 0.1% in all cases, except with Tween 80, and that each of the formulations were clear, single phase systems, with the exception of the Tween 80 system, which produced a cloudy system.

TABLE 2

SURFACTANT DISSOLUTION IN BLENDS OF HFC-134a AND HFC-227

|  | Antarox 31R1 | Brij 30 | PEG 300 |
|---|---|---|---|
| Weight of SAA (g) | 0.031 | 0.031 | 0.030 |
| Weight of HFC-227 (g) | 14.858 | 14.912 | 15.058 |
| Weight of HFC134a (g) | 14.932 | 15.084 | 15.102 |
| % w/w of SAA | 0.104 | 0.103 | 0.099 |
| % w/w of HFC-227 | 49.824 | 49.662 | 49.877 |
| Solution at 0 hrs. Temp. = 22° C. | Clear Solution | Clear Solution | Clear Solution |

|  | Transcutol | Tween 20 | Tween 80 |
|---|---|---|---|
| Weight of SAA (g) | 0.030 | 0.030 | 0.031 |
| Weight of HFC-227 (g) | 14.895 | 15.163 | 14.981 |
| Weight of HFC134a (g) | 15.051 | 14.925 | 14.863 |
| % w/w of SAA | 0.100 | 0.100 | 0.104 |
| % w/w of HFC-227 | 49.69 | 50.345 | 50.146 |
| Solution at 0 hrs. Temp. = 22° C. | Clear Solution | Clear Solution | Cloudy Solution |

Tables 1 and 2 indicate that surfactants with HLB values greater than 9.6 can be used in MIDI formulations which use HFC-227 alone or in combination with other propellants such as HFC- 134a. The preferred surfactants for use in MDIs include polyoxyethylene sorbitan monolaurate (Tween 20), polyoxyethylene sorbitan mono-oleate (Tween 80), polyethylene glycol 300 (PEG 300), Antarox 31R1, Brij 30, and Transcutol since these surfactants are generally regarded as safe (GRAS).

Those skilled in the art will recognize that surface active agents are occasionally mixed together in order to improve the quality of the surfactant film absorbed at solid:liquid and liquid:liquid interfaces of pharmaceutical importance, specifically with the purposes of improving the stability of the dispersed systems. This subject is discussed in Martin et al., *Physical Pharmacy,* 3rd Ed., Lea & Febiger, Philadelphia, Pa., pp. 544–573, 1983, where it is noted that surfactant films formed by admixtures of molecules sometimes have improved properties over either of the single components used alone. While this invention has been described in terms of the use of a single surfactant in the MDI formulation, those skilled in the art will recognize that mixtures of surfactants, and particularly the preferred surfactants identified above, can be used within the practice of the present invention.

In a preferred embodiment, the MDI formulations which employ HFC-227 and the polar surfactant with the high HLB value will be formulated in the same manner as the current CFC based MDIs (e.g., cold filling, pressure filling, etc.) and with the components in approximately the same proportions (e.g., greater than 90% by weight propellant or propellant blend (where HFC-227 constitutes substantially 50% or more of the blend), less than 5% by weight and most preferably less than 1% by weight micronized drug (usually less than 5 μm in diameter), and less than 5% by weight surfactant). A wide variety of drugs may be employed in the MDI formulations of the present invention including anti-allergics (e.g., cromolyn sodium), bronchodilators (e.g., albuterol), steroids (e.g., beclomethasone dipropionate), analgesics, antihistamines, antibiotics (e.g., penicillin), hormones (e.g., cortisone) and therapeutic proteins and peptides (e.g., insulin).

While the invention has been described in terms of its preferred embodiments, those skilled in the art will recognize that the invention can be practiced with modification within the spirit and scope of the appended claims.

We claim:

1. An alcohol-free aerosol formulation for use in a metered does inhaler, consisting essentially of:

greater than 90% by weight of 1,1,1,2,3,3,3-heptafluoropropane, said 1,1,1,2,3,3,3-heptafluoropropane being the sole propellant and excipient which is not a surfactant in said aerosol formulation;

less than 5% by weight of micronized drug particles; and less than 5% by weight of at least one polar surfactant having a hydrophilic-lipophilic balance value greater than 9.6, said aerosol formulation being alcohol-free.

2. The aerosol formulation of claim 1 wherein said polar surfactant is selected from the group consisting of polyoxyethylene sorbitan monolaurate, polyoxyethylene sorbitan mono-oleate, polyethylene glycol 300, propoxylated polyethylene glycol, polyoxyethylene 4 lauryl ether, and diethylene glycol monoethyl ether.

3. The aerosol formulation of claim 2 wherein said polar surfactant is polyoxyethylene sorbitan monolaurate.

4. The aerosol formulation of claim 2 wherein said polar surfactant is polyoxyethylene sorbitan mono-oleate.

5. The aerosol formulation of claim 2 wherein said polar surfactant is polyethylene glycol 300.

6. The aerosol formulation of claim 2 wherein said polar surfactant is propoxylated polyethylene glycol.

7. The aerosol formulation of claim 2 wherein said polar surfactant is polyoxyethylene 4 lauryl ether.

8. The aerosol formulation of claim 2 wherein said polar surfactant is diethylene glycol monoethyl ether.

9. The aerosol formulation of claim 1 further comprising at least a second polar surfactant having a hydrophilic-lipophilic balance value greater than 9.6 wherein a combination of said first and second surfactant comprise less than 5% by weight.

10. An alcohol-free aerosol formulation for use in a metered dose inhaler, consisting essentially of:

greater than 90% by weight of a propellant blend consisting of 1,1,1,2-tetrafluoroethane and 1,1,1,2,3,3,3-heptafluoropropane, said propellant blend constituting the only excipients which are not a surfactant in said aerosol formulation;

less than 5% by weight of micronized drug particles; and less than 5% by weight of at least one polar surfactant having a hydrophilic-lipophilic balance value greater than 9.6, said aerosol formulation being alcohol-free.

11. The aerosol formulation of claim 10 wherein said polar surfactant is selected from the group consisting of polyoxyethylene sorbitan monolaurate, polyethylene glycol 300, propoxylated polyethylene glycol, polyoxyethylene 4 lauryl ether, and diethylene glycol monoethyl ether.

12. The aerosol formulation of claim 10 wherein said polar surfactant is polyoxyethylene sorbitan monolaurate.

13. The aerosol formulation of claim 10 wherein said polar surfactant is polyethylene glycol 300.

14. The aerosol formulation of claim 10 wherein said polar surfactant is propoxylated polyethylene glycol.

15. The aerosol formulation of claim 10 wherein said polar surfactant is polyoxyethylene 4 lauryl ether.

16. The aerosol formulation of claim 10 wherein said polar surfactant is diethylene glycol monoethyl ether.

17. The aerosol formulation of claim 10 further comprising at least a second polar surfactant having a hydrophilic-lipophilic balance value greater than 9.6 wherein a combination of said first and second surfactant comprise less than 5% by weight.

18. An alcohol-free aerosol formulation for use in a metered dose inhaler, consisting essentially of:

greater than 90% by weight of a propellant blend consisting of at least 50% 1,1,1,2,3,3,3-heptafluoropropane and a second propellant, said propellant blend constituting the only excipients which are not a surfactant in the MDI formulation;

less than 5% by weight of micronized drug particles; and less than 5% by weight of at least one polar surfactant having a hydrophilic-lipophilic balance value greater than 9.6, said aerosol formulation being alcohol-free.

19. The aerosol formulation of claim 18 wherein said polar surfactant is selected from the group consisting of polyoxyethylene sorbitan monolaurate, polyethylene glycol 300, propoxylated polyethylene glycol, polyoxyethylene 4 lauryl ether, and diethylene glycol monoethyl ether.

20. The aerosol formulation of claim 10 further comprising at least a second polar surfactant having a hydrophilic-lipophilic balance value greater than 9.6 wherein a combination of said first and second surfactant comprise less than 5% by weight.

* * * * *